US010426370B2

(12) United States Patent
Jones et al.

(10) Patent No.: US 10,426,370 B2
(45) Date of Patent: Oct. 1, 2019

(54) ELECTROMYOGRAPHIC CONTROLLED VEHICLES AND CHAIRS

(71) Applicant: Limbitless Solutions, Inc., Orlando, FL (US)

(72) Inventors: Brendan Jones, Apopka, FL (US); Albert Manero, II, Orlando, FL (US); John Sparkman, Orlando, FL (US)

( * ) Notice: Subject to any disclaimer, the term of this patent is extended or adjusted under 35 U.S.C. 154(b) by 180 days.

(21) Appl. No.: 15/361,372

(22) Filed: Nov. 26, 2016

(65) Prior Publication Data

US 2018/0147099 A1 May 31, 2018

(51) Int. Cl.

| | |
|---|---|
| ***A61G 5/04*** | (2013.01) |
| ***A61B 5/0488*** | (2006.01) |
| ***B60K 1/00*** | (2006.01) |
| ***B60L 15/00*** | (2006.01) |

(52) U.S. Cl.

CPC ........... *A61B 5/0488* (2013.01); *A61G 5/041* (2013.01); *B60K 1/00* (2013.01); *B60L 15/00* (2013.01); *A61G 2203/18* (2013.01); *A61G 2203/70* (2013.01); *B60L 2200/34* (2013.01)

(58) Field of Classification Search

CPC .... A61B 5/0488; A61G 5/04; A61G 2203/22; A61G 2203/30

See application file for complete search history.

(56) References Cited

U.S. PATENT DOCUMENTS

| | | | | |
|---|---|---|---|---|
| 2015/0053490 A1* | 2/2015 | Santagata | A61G 5/06 | 180/65.1 |
| 2016/0121956 A1* | 5/2016 | Mizuno | A61G 5/045 | 701/22 |
| 2016/0250930 A1* | 9/2016 | Collins | B60L 15/2036 | 701/22 |
| 2018/0107275 A1* | 4/2018 | Chen | G06F 3/015 | |

OTHER PUBLICATIONS

Kyuwan Choi, M. Sato and Y. Koike, "A new, human-centered wheelchair system controlled by the EMG signal," The 2006 IEEE International Joint Conference on Neural Network Proceedings, Vancouver, BC, 2006, pp. 4664-4671. (Year: 2006).*

G. Jang and Y. Choi, "EMG-based continuous control method for electric wheelchair," 2014 IEEE/RSJ International Conference on Intelligent Robots and Systems, Chicago, IL, 2014, pp. 3549-3554. doi: 10.1109/IROS.2014.6943058 (Year: 2014).*

* cited by examiner

*Primary Examiner* — Robert T Nguyen

(74) *Attorney, Agent, or Firm* — Maxwell L. Minch; GrayRobinson, P.A.

(57) ABSTRACT

The present invention is intended to provide an EMG signal controller or a wheelchair using an EMG signal controller to allow full vehicular direct drive control, and wheelchair accessory control, by using one or more EMG sensors applied to certain muscles of a subject, and translating the movement of the muscles of the subject that the EMG sensors are connected, to electrical signals causing for the operation of a motorized wheelchair. The controller and wheelchair are designed specifically for paralyzed individu- (Continued)

als with limited motion, but may be used by any subject with or without any physical or nervous system disabilities. The present invention further provides an emergency stop which is activated in the event that the subject using the wheelchair experiences a seizure or other neurological shock.

7 Claims, 2 Drawing Sheets

ELECTROMYOGRAPHIC CONTROLLED VEHICLES AND CHAIRS

FIELD OF INVENTION

The present invention relates to electric vehicles and wheelchairs for use by subjects. More particularly, the present invention relates to electric wheelchairs interfacing with the electromyographic (EMG) signals from subjects to enable an EMG controlled electric vehicle or wheelchair.

BACKGROUND

Disabled persons often encounter problems with movement and mobility, particularly when it comes to maneuvering devices such as wheelchairs. In addition, for both medical and entertainment purposes, hand-free controlled vehicles and wheelchairs have been sought after to offer alternative solutions relating to particular needs of individuals. Many solutions have been provided to provide advances in electric mobility, particularly with maneuvering electronic wheelchairs, but each solution has introduced new problems in the art.

Existing solutions in the art have many shortcomings which have plagued technologies set out to solve similar problems. One attempt includes "sip and puff", which makes use of an air pressure induced switch. However, the sip and puff systems are invasive and requires complete user focus and attention. In addition, sip and puff motorized systems do not allow for fluid movement. Moreover, in the event of a seizure or other neurological shock, nothing in the sip and puff system stops the system, and to include such a feature in a sip and puff system would require a constant sip or puff control during the operation of the wheelchair, which could cause other issues.

Some attempts result in a delayed or prolonged reaction time to get to every pre-programmed direction, thus it becomes burdensome and provides less ubiquitous movement. The predetermined positions and angles pre-programmed into the motion controller become user unfriendly and a burden for a user to use.

Other solutions use a visual indicator that cycles through a group of predetermined commands, which one must try and stop the visual indicator on the command or control they desire. In addition once a direction is selected on the visual indicator the visual indicators remains activate for a predetermined amount of time when activated. The features limit the control a user has, and in many situation can be dangerous to a user. For example, in these configurations if a user is close to a staircase they would want to be able to directly control the amount of time the controller is activated and not have it based on a predetermined time. This can cause a delay in control time as it will take additional time to cycle from forward position to reverse position.

Yet additional solutions attempt to use an indirect controller where the user needs to look at the controller in order to know which direction he/she will go. This makes the user take their eyes off their surroundings while driving. This solution is often disrupted if there are loud noises in the environment.

Thus there remains an unmet need for a ubiquitous EMG signal controller that allows a user to provide signals without having to direct their attention to any visual or audio indication in order to provide desired motion signals to an EMG motion controller.

It is appreciated that the disabled usually have neurological or central nervous disabilities to accompany their physical or skeletal or muscular disabilities, thus it is common that disabled users are subject to seizures or other neurological shocks and involuntary movements. The current solutions do not include the ability to provide an emergency stop in case a user has seizure or other medical condition that causes user to lose control of muscles. Thus there remains an unmet need to provide an EMG control system that stops movement in the event of erratic muscle movements.

Finally, other solutions prove difficult to integrate into other wheelchair controls/devices such as the device can only use the pre-set commands listed on the visual indicator. Thus retro-fitting an existing chair becomes impossible and often adds additional elements causing failure. Thus there further remains an unmet need for a system that can be included in a kit for retro-fitting an existing motor vehicle or wheelchair.

To date no solution has been offered to overcome any of the shortcoming described in the industry of electronic wheelchairs for disabled persons. Consumers are often frustrated by the lack of any solutions to this problem, and consequently there remains an unmet need.

SUMMARY

The present invention provides an EMG controlled motion controller which is controlled directly by the input of a sensor as opposed to being conformed to a pre-programmed input. The present invention minimizes device reaction time by allowing the sensors to directly command the wheelchair direction using a combination of sensor activations (all using no more than 2 simultaneous activations for each command). Since the device is directly controlled by the wheelchair the user is directly using their muscles, which through the use of the inventive controller, determines the speed and direction the wheelchair will move.

The present invention further provides an emergency stop in the event of a seizure, neurological shock, or other cause of involuntary muscle movement. The E-stop is activated upon receipt of a signal and as a result of the received EMG signals, the controller communicates the wheelchair to stop. The stop signal can be intentionally triggered by the user, and also triggers when an uncontrolled muscle impulse is provided to the EMG signal controller.

Finally the present invention provides the ability to create additional commands, other than direction and speed, such as adjusting leg rest, height of wheelchair, angle of wheelchair, horn, and other accessories.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION

Figure 1:
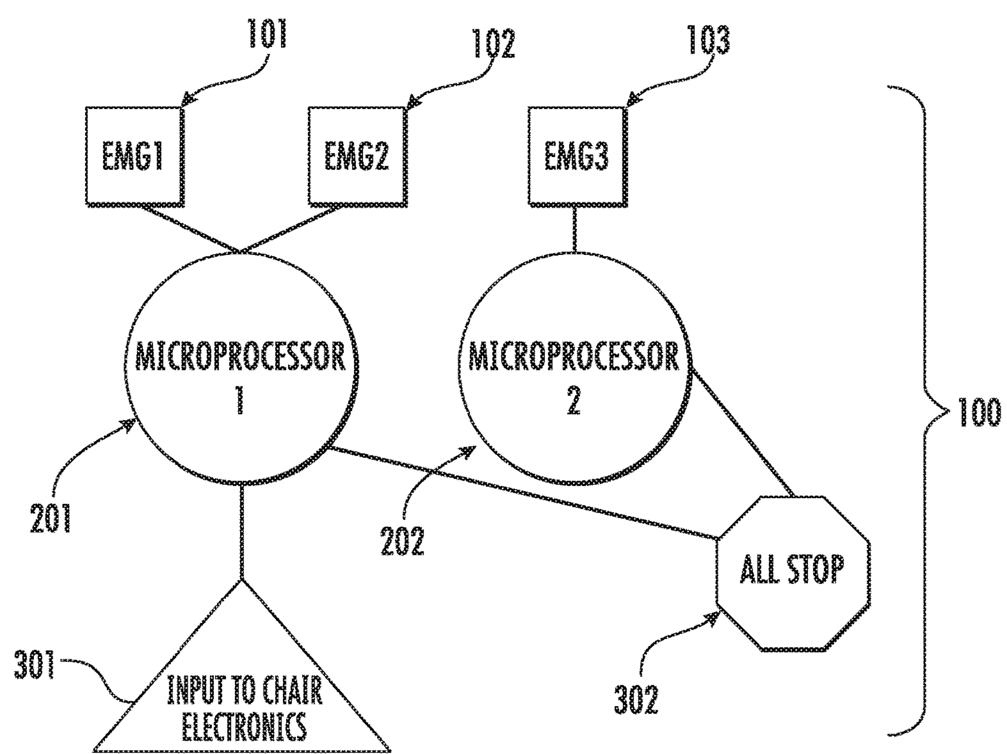
FIG. 1 is an illustration of one embodiment of the EMG Sensor and EMG Signal Controller configuration.
Figure 2:
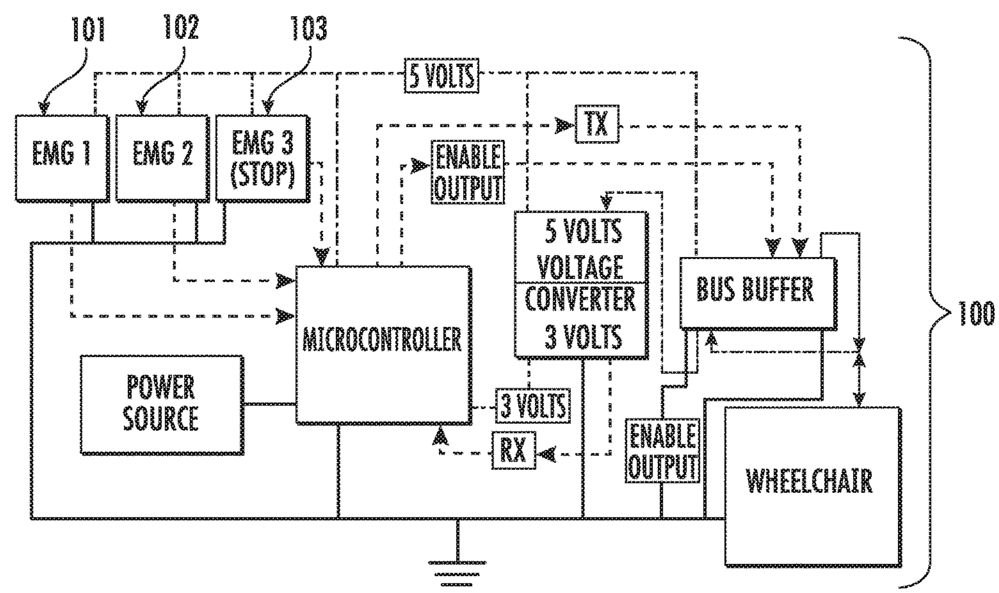
FIG. 2 is an illustration of a detailed view of one embodiment of a motor controlled wheelchair making use of an EMG signal controller for controlling the wheelchair using EMG sensors.

The present invention is intended to provide full vehicular direct drive control by a user, made possible by the use of one or more EMG sensors applied to a user. Without intending to limit the invention, in one example face muscles are used for providing input signals to the EMG sensors and ultimately controlling the motorized vehicle. The present invention is intended for subjects suffering from paralysis or significant physical disabilities, however nothing herein is intended to limit who may use an EMG controlled vehicle, including those individuals not suffering from any physical or neurological disabilities.

The following detailed description is merely exemplary in nature and is in no way intended to limit the scope of the invention, its application, or uses, which may vary. It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Generally

The present invention provides an electro-myographic (EMG) controlled electronic wheelchair which includes a motor controlled wheelchair, at least one EMG sensor and at least one EMG signal controller. The present invention includes features which provide for direct control of EMG sensors to a controlling unit of a wheelchair.

The present invention further provides for an emergency stop feature which stops a wheel chair and returns the controls to neutral in the event of receiving a signal that the subject is having a seizure or some other neurological or physical shock. In at least one embodiment, the electronic stop feature is a result of an EMG signal from a non-controlling muscle group.

Further included in the present invention is the ability to control other electronic features of a motorized vehicle other than direction or motion. It is appreciated that most electronic vehicles include accessories such as horns, or electronic adjustments for the seat or other parts of the chair to make the use of the vehicle comfortable by a user.

Further included in the present invention is the ability to retrofit an existing motorized vehicle with the inventive EMG signal controller in place of the existing joystick or controllers.

The present invention allows for direct drive using the EMG signals received by the EMG controller, and does not require pre-programmed gestures. The EMG signal controller reacts, and communicated with the electronic vehicle, based on the length of muscle activation.

Motor Controlled Vehicle

The motor controlled vehicle includes a chair for holding at least one person, one or more motors for controlling one or more wheels, and one or more wheels. In some embodiments the motor controlled vehicle is a wheelchair, but any motor controlled vehicle may be used for the present invention, such as a Segway, an electric scooter, an electronic golf cart, an electric car, an electric skateboard, or combinations thereof. For the avoidance of doubt, nothing herein is intended to limit the electronic vehicle intended to be used in the present invention.

One embodiment of the present invention includes a motor controlled vehicle making use of the EMG signal controller, while at least one embodiment of the wheelchair includes a joystick or controller, which is removed and replaced by the inventive EMG signal controller, including the appropriate cable interfaces and impedance matching between the EMG signal controller and the motorized vehicle.

It is appreciated that while a motorized vehicle is operated by motors which require large amount of electrical power to operate, that the motors are controlled by a motion controlling unit or circuit which is a low voltage circuit that activates switches, servos, or signals to other controllers in the motorized vehicle to perform a specific function that is received by the motion controlling unit. It is further appreciated that the interface which distributes the low voltage motion signals to the motors or the particular controllers or switches for the different motors, that in some embodiments, the same unit also distributes or communicated signals to the accessories of the motor vehicle.

The motion controlling unit distributes the communicated motion signals from the EMG signal controller to the electronic wheel chair. Distributing the signals from the EMG signal controller to the wheelchair may be accomplished in a number of ways. In one embodiment, the electric signals are translated directly to the motion controlling unit (or a motion distribution center) of an electronic wheel chair which send commands to the one or more wheel motors and servos of the electronic vehicle or wheelchair.

EMG Sensor

The electro-myographic (EMG) sensors are used to detect the electrical potential generated by the cells of a subject. These cells include muscle cells or neurological cells. It is intended as part of this invention that a subject deliberately interacts with, or commands, the EMG sensors. The electrical signals from the EMG sensors are then communicated and interpreted by the EMG Signal controller.

In at least one embodiment of the invention includes at least one EMG sensor for interacting with a subject to control the movement and to maneuver an electric wheelchair. It is appreciated that to improve signal accuracy, redundancy and to provide a higher resolution of movement and maneuvering responses that a plurality of EMG sensors are used to communicate between a subject and an EMG Signal Controller. In certain embodiments, the invention uses two electro-myographic sensors (muscle voltage sensor) in tandem on sets of facial muscles or upper body muscle sets to directly drive a powered vehicle or wheelchair. In at least one embodiment three sensors are used, where a third sensor is placed on an unused muscle group that would involuntarily flex or move in the event of a seizure or some other neurological or physical shock. The use of this third EMG sensor allows to provide an emergency stop to the wheel chair or the motion controlling unit of the wheelchair when a signal is received by the third sensor. While the above description contemplates one, two or three sensors, nothing herein is intended to fix or limit the number of EMG sensors which may be used to provide an input to the controller. It is appreciated that additional sensors may be used to provide a higher resolution EMG signal to the EMG signal controller.

EMG Signal Controller

The EMG signal controller receives the EMG signals from the EMG sensors and communicates a usable output to the wheelchair, or the motion controlling unit of the wheelchair. FIG. 1 provides at least one embodiment of the EMG signal controller. The EMG sensors send signals to the input of the EMG signal controller, which directly communicates the received signals to a central processing unit (CPU), a computer, of a microcontroller.

In at least one embodiment, the raw EMG signal is used, and when the raw EMG signal goes above a pre-set threshold a command/activation input, the input is translated using one or more algorithms to a command (representing speed, direction, or operation of an accessory). The EMG signal controller communicates the translated signal to electronics of the electronic vehicle to cause the electronic vehicle to activate one or more motors or accessories.

One unique feature of the present invention, and in embodiments which make use of a plurality of EMG sensors, is that when multiple raw EMG signals are received above the user's customized thresholds, different user commands can be activated. As a result the device can be customized to each power wheelchair/vehicle and the output commands can be changed according to the application and user needs.

It should be appreciated that in some embodiments EMG signals must be above a user's customized thresholds. Because the physiology of each human is different, and more so with those who have debilitation injuries or disorders, the strength of an EMG signal from user to user may vary. Moreover, nearby muscles or muscle group may be sensed by an adjacent EMG sensor. Therefore, it is intended that the EMG signals being received by a user be intentional and directly relate to a user's will to make a certain command, instead of an inadvertent command. As a result, in some embodiments, the EMG signal controller is calibrated to each user. In some embodiments, the EMG controller includes a series of software commands for recording the EMG signals from a user in order to calibrate the system and establish threshold EMG signal intensity for the particular user. In some embodiments, pre-calibration is conducted upon startup and accounts for intrinsic user specific skin resistance and baseline muscle energetics.

In at least one embodiment the 101 a first EMG sensor controls left movement, a 102 second EMG sensor controls right movement, and a 103 third EMG sensor controls 302 an emergency stop. As provided earlier, in embodiments incorporating an emergency stop, an EMG sensor is intended to be attached to a series of muscles or muscle groups that would only be used or flexed in the event of a seizure or some other neurological of physical shock. In such an embodiment, the 201 first microprocessor processes the 101,102 EMG signal 1 and 2, while the 202 second microprocessor Processes 103 EMG signal 3 for the 302 E-stop. When 103 signal 3 is activated 202 microprocessor 2 will stop all commands in microprocessor 1. Provided there is no 302 emergency stop signal, the 301 controller takes all output signals from microprocessor 1 and sends it as an input to the wheelchair/vehicle.

In at least one embodiment, the EMG signal controller receives at least two inputs with a single output from a microcontroller, a user may drive in any direction, or set of directions, directly without interference or pre-programming. It should be appreciated that a dual input from EMG sensors with a single output, allows for vehicular control with only facial muscles.

In at least one embodiment, the EMG signal controller provides a single output to be received by the electronic vehicle. The single output from microcontroller and signal processing code, with pattern recognition, allows for direct input to the electronic vehicle for direct user control.

In some embodiments the EMG signal controller includes an on board power supply. The power supply may consist of any power supply known in the art. In some embodiments the power supply is a battery or an array of batteries. In some embodiment, the power supply is a power source received from the wheel chair. The power to the EMG signal controller may be from a separate cable, or may be received from the output cable interfacing the EMG signal controller to the electronic vehicle.

Conversion Kits

A kit for converting an electronic wheelchair to an electro-myographic controlled wheelchair is provided. The kit includes an EMG signal controller and an EMG sensor array containing at least one EMG sensor for connecting to a patient. It is appreciated that the output of the kit is intended to directly interface with the existing electronics of the electronic vehicle, such as the same plug that is in place for interfacing with the joystick of the wheelchair. The joystick that accompanies the electronic vehicle, particularly wheelchairs, is unplugged, and subsequently removed. The EMG signal controller is put in the place of the previous joystick, and the cable that was removed from the joystick is placed into the EMG signal controller.

EXAMPLES

It is to be understood that while the invention has been described in conjunction with the detailed description herein, the foregoing description is intended to illustrate and not limit the scope of the invention, which is defined by the scope of the appended claims. Other aspects, advantages, and modifications are within the scope of the following claims.

Example 1

Figure 3:
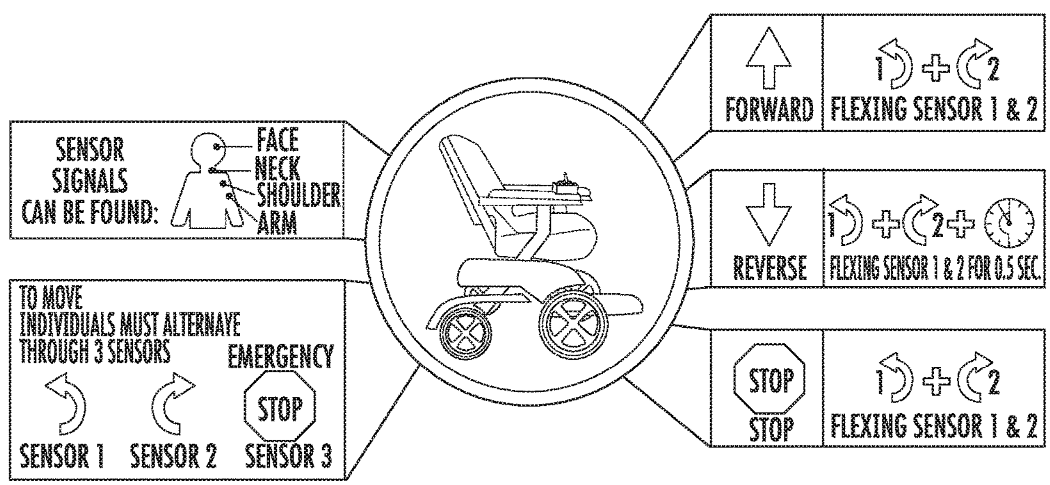
FIG. 3 illustrates the EMG sensor inputs and subsequent control actions in at least one embodiment of the invention.

An electro-myographic controlled wheel chair is provided that includes a motor controlled wheelchair, 3 EMG sensor and an EMG signal controller adapted for receiving three EMG signals. EMG sensor 1 and 2 are attached to the face of the individual. The third EMG sensor is attached between the shoulder blades. EMG sensor 1 controls movement to the right. EMG sensor 2 controls movement to the left. Impulse activation of EMG sensor 1 and EMG sensor 2 allows for forward movement, while intermittent facial movements to sensor 1 and sensor 2 allow for a user to control the movement of the wheelchair. If the user activates sensors 1 and 2 for a period of time (0.5 seconds in this example), the wheelchair is moved in reverse. Upon the intermittent receipt of both signals 1 and 2 further cause the chair to stop. FIG. 3 is illustrative of such an algorithm. Upon the receipt of an EMG signal from the third sensor the signal stops

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. An electro-myographic (EMG) signal controller for receiving and translating one or more signals from one or more EMG sensors to an electrical signal communicated to a motorized wheelchair to control a speed and direction of the motorized wheelchair based on the signals received by the EMG sensors, the controller comprising:

an input for receiving one or more signals from one or more EMG sensors attached to a skin surface about one or more muscles of a wheelchair occupant; an output for interfacing and translating the received EMG signals to the wheelchair; and at least one computer for receiving one or more signals from one or more EMG sensors and providing one or more electrical signals to the wheelchair, wherein said EMG signals received by the wheelchair cause one or more motors or motor controllers of the wheelchair to activate based on the one or more EMG signals received from the one or more EMG sensors and wherein the computer provides an electrical signal to the wheelchair to control the direction, speed, and horn of the wheelchair.

2. The EMG signal controller of claim 1 wherein said EMG signal is translated to one or more electrical signals to be received using an algorithm that is programmed based on preferences of a subject using the wheelchair.

3. The EMG signal controller of claim 1 further comprising an input from the wheelchair to the EMG signal controller to provide the EMG signal controller power.

4. The EMG signal controller of claim 1 further comprising an internal power supply to provide the EMG signal controller power.

5. An electro-myographic (EMG) controlled electronic wheelchair, the EMG wheelchair comprising:

at least one EMG sensor attached to a skin surface about one or more muscles of a wheelchair occupant;

a motor controlled wheelchair having one or more motors which control a direction and speed that the wheelchair will travel; and at least one EMG signal controller for receiving one or more signals from said EMG sensor and translating said EMG signals to a directional input which is communicated to the wheelchair wherein said signal controller controls the direction, speed, and horn of the wheelchair based on said EMG signals.

6. The EMG wheelchair of claim 5 wherein said EMG sensor is connected to a face, neck, shoulder, or arm of a subject travelling in the wheelchair, or combinations thereof.

7. The EMG wheelchair of claim 5 wherein said EMG signal controller further comprises a non-transitory computer-readable medium containing computer-readably instructions which, when executed, cause a computer to perform the process of interpreting EMG signals received by one or more EMG sensors and communicating the interpreted signals to a motion controlling circuit.

* * * * *